US009827254B2

(12) United States Patent
Richter et al.

(10) Patent No.: US 9,827,254 B2
(45) Date of Patent: *Nov. 28, 2017

(54) METHOD OF TREATING ACUTE CORONARY SYNDROMES

(71) Applicant: BIOrest Ltd., Tel Aviv (IL)

(72) Inventors: Yoram Richter, Ramat Hasharon (IL); Elazer R. Edelman, Brookline, MA (US); Gershon Golomb, Efrat (IL); Haim D. Danenberg, Mevaseret Zion (IL)

(73) Assignee: BIOrest Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,395

(22) Filed: Oct. 27, 2016

(65) Prior Publication Data

US 2017/0100415 A1    Apr. 13, 2017

Related U.S. Application Data

(63) Continuation of application No. 10/871,488, filed on Jun. 18, 2004, now Pat. No. 9,498,488, which is a
(Continued)

(51) Int. Cl.
A61K 9/127        (2006.01)
A61K 31/282       (2006.01)
(Continued)

(52) U.S. Cl.
CPC ............ *A61K 31/663* (2013.01); *A61K 9/127* (2013.01)

(58) Field of Classification Search
None
See application file for complete search history.

(56) References Cited

U.S. PATENT DOCUMENTS 4,067,971 A    1/1978  Francis et al.
4,216,211 A    8/1980  Francis
(Continued)

FOREIGN PATENT DOCUMENTS

DE    196 37 890 A1    3/1998
EP    0339237          11/1989
(Continued)

OTHER PUBLICATIONS

Afergan et al., "Delivery of Serotonin to the Brain by Monocytes Following Phagocytosis of Liposomes," Journal of Controlled Release 132 pp. 84-90 (2008).
(Continued)

*Primary Examiner* — Aradhana Sasan
(74) *Attorney, Agent, or Firm* — Cadwalader, Wickersham & Taft LLP

(57) ABSTRACT

The present invention relates to methods and compositions designed for the treatment or management of acute coronary syndromes, particularly, unstable angina and acute myocardial infarction. The methods of the invention comprise the administration of an effective amount of a formulation containing one or more therapeutic agents which specifically decreases or inhibits the activity of phagocytic cells and/or eliminates or diminishes the amount of phagocytic cells including, but not limited to, macrophages and monocytes. The formulations are specifically targeted to phagocytic cells. The invention also provides pharmaceutical compositions of formulations containing one or more therapeutic agents of the invention for administration to subjects currently suffering from or having recently suffered an acute coronary syndrome such as unstable angina and acute myocardial infarction.

15 Claims, 3 Drawing Sheets

Related U.S. Application Data continuation-in-part of application No. 10/607,623, filed on Jun. 27, 2003.

(51) Int. Cl.

| | | |
|---|---|---|
| *A61K 31/337* | (2006.01) | |
| *A61K 31/365* | (2006.01) | |
| *A61K 31/436* | (2006.01) | |
| *A61K 31/47* | (2006.01) | |
| *A61K 31/4745* | (2006.01) | |
| *A61K 31/513* | (2006.01) | |
| *A61K 31/56* | (2006.01) | |
| *A61K 31/60* | (2006.01) | |
| *A61K 31/616* | (2006.01) | |
| *A61K 31/66* | (2006.01) | |
| *A61K 31/663* | (2006.01) | |

(56) References Cited

U.S. PATENT DOCUMENTS

| | | | |
|---|---|---|---|
| 4,990,503 | A | 2/1991 | Isomura et al. |
| 4,997,454 | A | 3/1991 | Violante et al. |
| 5,096,717 | A | 3/1992 | Wirth et al. |
| 5,196,409 | A | 3/1993 | Breuer et al. |
| 5,312,954 | A | 5/1994 | Breuer et al. |
| 5,338,731 | A | 8/1994 | Breuer et al. |
| 5,356,887 | A | 10/1994 | Brener et al. |
| 5,492,926 | A | 2/1996 | Cullinan et al. |
| 5,527,538 | A | 6/1996 | Baldeschwieler |
| 5,652,227 | A | 7/1997 | Teronen et al. |
| 5,698,531 | A | 12/1997 | Nabel et al. |
| 5,733,564 | A | 3/1998 | Lehtinen |
| 5,741,514 | A | 4/1998 | Barenholz et al. |
| 5,746,223 | A | 5/1998 | Williams |
| 5,760,030 | A | 6/1998 | Bryant et al. |
| 5,776,429 | A | 7/1998 | Unger et al. |
| 5,792,885 | A | 8/1998 | Ham et al. |
| 5,811,118 | A | 9/1998 | Ostro et al. |
| 5,820,879 | A | 10/1998 | Fernandez et al. |
| 5,882,656 | A | 3/1999 | Bechard et al. |
| 5,932,563 | A | 8/1999 | Stokes et al. |
| 5,932,580 | A | 8/1999 | Levitzki et al. |
| 5,994,341 | A | 11/1999 | Hunter et al. |
| 6,030,639 | A | 2/2000 | Janoff et al. |
| 6,090,777 | A | 7/2000 | Hack et al. |
| 6,121,278 | A | 9/2000 | Jackson et al. |
| 6,139,871 | A | 10/2000 | Hope et al. |
| 6,245,757 | B1 | 6/2001 | Chopp et al. |
| 6,306,421 | B1 | 10/2001 | Kunz et al. |
| 6,432,413 | B1 | 8/2002 | Loeb |
| 6,719,998 | B1 | 4/2004 | Golomb et al. |
| 6,770,466 | B2 | 8/2004 | Shi et al. |
| 6,984,400 | B2 | 1/2006 | Golomb et al. |
| 7,008,645 | B2 | 3/2006 | Golomb et al. |
| 9,498,488 | B2 * | 11/2016 | Reynolds ............ A61K 9/127 |
| 2001/0031741 | A1 | 10/2001 | Ziegler et al. |
| 2002/0025313 | A1 | 2/2002 | Micklus et al. |
| 2002/0110588 | A1 | 8/2002 | Hope et al. |
| 2002/0160495 | A1 | 10/2002 | Mirochnitchenko et al. |
| 2002/0187184 | A1 | 12/2002 | Golomb et al. |
| 2002/0192157 | A1 | 12/2002 | Low et al. |
| 2003/0013686 | A1 | 1/2003 | Golomb et al. |
| 2003/0091547 | A1 | 5/2003 | Edelberg et al. |
| 2003/0100514 | A1 | 5/2003 | Ahotupa et al. |
| 2004/0265391 | A1 * | 12/2004 | Danenberg ............ A61K 9/127 424/490 |
| 2004/0266734 | A1 | 12/2004 | Danenberg et al. |

FOREIGN PATENT DOCUMENTS

| | | |
|---|---|---|
| EP | 0459318 | 12/1991 |
| WO | WO 88/00289 | 1/1988 |
| WO | WO 93/09790 | 5/1993 |
| WO | WO 96/20698 | 7/1996 |
| WO | WO 97/16170 | 5/1997 |
| WO | WO 97/33552 | 9/1997 |
| WO | WO 97/43437 | 11/1997 |
| WO | WO 98/31359 | 7/1998 |
| WO | WO 99/17740 | 4/1999 |
| WO | WO 99/38998 | 8/1999 |
| WO | WO 00/03677 | 1/2000 |
| WO | WO 00/21540 | 4/2000 |
| WO | WO 00/34293 | 6/2000 |
| WO | WO 00/56866 | 9/2000 |
| WO | WO 00/64516 | 11/2000 |
| WO | WO 00/69412 | 11/2000 |
| WO | WO 00/69503 | 11/2000 |
| WO | WO 01/74337 | 10/2001 |
| WO | WO 02/083096 A1 | 10/2002 |
| WO | WO 03/020243 | 3/2003 |
| WO | WO 03/086351 | 10/2003 |
| WO | WO 03/089568 | 10/2003 |
| WO | WO 03/097696 | 11/2003 |
| WO | WO 2005/002545 | 1/2005 |
| WO | WO 2005/044175 | 5/2005 |

OTHER PUBLICATIONS

Allaire, et al., "Endothelial Cell Injury in Cardiovascular Surgery: The Intimal Hyperplastic Response," *Ann. Thorac. Surg.*, 63(2):582-91 (1997).

Anderson, et al., "A review of randomized trials comparing coronary angioplasty and bypass grafting," *Curr-Opin-Cardiol.*, 11(6):583-90 (1996).

Arefieva, et al., "Monocyte Integrin Expression and Monocyte-Platelet Complex Formation in Humans with Coronary Restenosis," *Clin. Exp. Pharm. Physio.*, 28:804-8 (2001).

Athlin et al., "Phagocytosis of Yeast Cells by Monocytes: Effects of Fluorouracil, Doxorubicin and Mitomycin," European Journal of Surgical Oncology, 1987, vol. 13, No. 1 p. 51-55.

Beers and Berkow, "The Merck Manual of Diagnosis and Therapy," Merck Research Laboratories, Whitehouse Stations, 1999.

Bellah, et al., "Idiopathic arterial calcification of infancy: Prenatal and postnatal effects of therapy in an infant," *The Journal of Pediatrics*, 121(6):930-3 (1992).

Benford, et al., "Farnesol and Geranylgeraniol Prevent Activation of Caspases by Aminobisphosphonates: Biochemical Evidence for Two Distinct Pharmacological Classes of Bisphosphonate Drugs," *Mol. Pharmacol.*, 56:131-140 (1999).

Bergh, et al., "Liposome-mediated macrophage depletion: an experimental approach to study the role of testicular macrophages in the rat," *J. Endocrinol.*, 136:407-13 (1993).

Biewenga, et al., "Macrophage depletion in the rat after intraperitoneal administration of liposome-encapsulated clodronate: depletion kinetics and accelerated repopulation of peritoneal and omental macrophages by administration of Freund's adjuvant," *Cell. Tissue Res.*, 280:189-196 (1995).

Bogdan et al, "Taxol, a microtubule-stabilizing antineoplastic agent, induces expression of tumor necrosis factor α and interleukin-1 in macrophages." Jounral of Leukocyte Biology, vol. 52, Jul. 1992 pp. 119-121.

Bohm, et al., "Exogenous Hepatitis B Surface Antigen Particles Processed by Dendritic Cells or Macrophages Prime Murine MHC Class I-Restricted Cytotoxic T Lymphocytes In Vivo," *J. Immunol.*, 155:3313-21 (1995).

Bolli, et al., "Evidence That Late Preconditioning Against Myocardial Stunning in Conscious Rabbits Is Triggered by the Generation of Nitric Oxide," *Circulation Res.*, 81:42-52 (1997).

Boras, et al., "Diabetes and Coronary Heart Disease," *Endocrinology and Metabolic Diseases*, 31-4:199-208 (2002).

Buiting, et al., "Liposomes as antigen carriers and adjuvants in vivo," *Res. Immunol.*, 143:541-8 (1992).

Cendejas-Santana et al., "Progesterone Crystallization from a Solvent: a New Procedure," Mat. Res. Innovat 6: 252-255 (2002).

Cipollone et al., "Elevated Circulating Levels of Monocyte Chemoattractant Protein-1 in Patients with Restenosis After Coronary Angioplasty", 2001, Arterioscler Thromb Vasc Biol, vol. 21, pp. 327-334.

(56) References Cited

OTHER PUBLICATIONS

Cohen, et al., "Synthesis and Preclinical Pharmacology of 2-(2-Aminopyrimidinio) Ethylidene-1, 1-Bisphosphonic Acid Betaine (ISA-13-1)—A Novel Bisphosphonate," *Pharma. Res.*, 16(9):1399-1406 (1999).
Cooper et al., "Rapamycin but not FK506 Inhibits the Proliferation of Mononuclear Phagocytes Induced by Colony-Stimulating Factors," Transplantation, vol. 57, No. 3, p. 433-439, 1994.
Danenberg et al., "Macrophage Depletion by Clodronate-Containing Liposomes Reduces Neointimal Formation After Balloon Injury in Rats and Rabbits," Circulation: Journal of the American Heart Association, pp. 599-605, Jul. 30, 2002.
Daoud, et al., "The effect of ethane-1-hydroxy-1, 1-diphosphonate (EHDP) on necrosis of atherosclerotic lesions," *Atherosclerosis*, 67:41-8 (1987).
Definition of opsonization by the Free Dictionary, retrieved from http://www.thefreedictionary.com/opsonization on Nov. 28, 2014, pp. 1-2.
Donbrow, "Microcapsules and Nanoparticles in Medicine and Pharmacy," CRC Press, Boca Raton, FL, pp. 1-347 (1992).
European Search Report dated Jan. 22, 2008 for EP 04 785 964.0 which claims priority to related U.S. Appl. No. 10/607,623.
Extended European Search Report and Opinion for EP 100106.0-1219 (published as EP 2266536) dated Sep. 17, 2012.
Fisher, et al., "Alendronate mechanism of action: geranylgeraniol, an intermediate in the mevalonate pathway, prevents inhibition of osteoclast formation, bone resorption, and kinase activation in vitro," *Cell Biol.*, 96:133-8 (1999).
Fleisch, "Bisphosphonates in bone disease," Parthenon Publishing Group Inc., pp. 184-210 (1997).
Flora, "Comparative Antiinflammatory and Bone Protective Effects of Two Diphosphonates in Adjuvant Arthritis," *Arthritis Rheum.*, vol. 22(4): 340-346 (1979).
Frith, et al., "The Molecular Mechanism of Action of the Antiresorptive and Antiinflammatory Drug Clodronate: Evidence for the Formation In Vivo of a Metabolite That Inhibits Bone Resorption and Causes Osteoclast and Macrophage Apoptosis," *Arth. Rheum.*, 44:2201-2210 (2001).
Gaytan, et al., "In vivo manipulation (depletion versus activation) of testicular macrophages: central and local effects," *J. Endocrinol.*, 150:57-65 (1996).
Gennaro, "Parenteral Preparations," *Remington: The Science and Practice of Pharmacy*, 20th Ed., Ch. 41, pp. 780-920 (2000).
Goldmann, et al., "Risk Stratification in Acute Coronary Syndrome," *Herz*, vol. 26, Supplement 1, pp. S24-S29, Background Section, Mar. 2001.
Gottsauner-Wolf, et al., "Influence of local delivery of the protein tyrosine kinase receptor inhibitor tyrphostin-47 on smooth-muscle cell proliferation in a rat carotid balloon-injury model," *Am. Heart J.*, 19:347-56 (1996).
Hamon, et al., "Restenosis after coronary angioplasty," *Eur. Heart J.*, 16:33-48 (1995).
Herrman, et al., "Pharmacological Approaches to the Prevention of Restenosis Following Angioplasty," *Drugs*, 46(1):18-52 (1993).
Hyvonen, et al., "Influence of dichloromethy bisphosphonate on the in vitro phagocytosis of hydroxyapatite particles by rat peritoneal exudate cells: an electron microscopic and chemiluminescence study," *Ann. Rheum. Dis.*, vol. 51: 203-209 (1992).
Iimuro et al., "Improvement of Survival Rate in Endotoxin Shock Model Rat by Administration of GdC13, Inhibitor of Liver Macrophage Phagocytosis," Digestive Organ and Immunology, No. 26, 1992, pp. 186-191.
International Search Report and Written Opinion dated Dec. 15, 2004 for corresponding application PCT/US2004/020487.
International Search Report and Written Opinion dated Dec. 23, 2005 for related application PCT/US2004/020536.
International Search Report and Written Opinion dated Jul. 29, 2008 for related application PCT/IB06/02028.
Jalowy, et al., "AT1 receptor blockade in experimental myocardial ischemia/reperfusion," *Basic Res. Cardiol.*, 93(2):85-91 (1998).

Kramsch, et al., "The Effect of Agents Interfering with Soft Tissue Calcification and Cell Proliferation on Calcific Fibrous-Fatty Plaques in Rabbits," *Circulation Res.*, 42(4):562-570 (1978).
Kunitomo et al., "Experimental Induction of Athero Sclerosis in guinea-Pigs Fed a Cholesterol Vitamin D-2-Rich Diet," 1983.
Aikawa, Masanori, "Vascular Biology of the Acute Coronary Syndromes," Cardiovascular Division. Department of Medicine, Brigham and Women's Hospital, Harvard Medical School, Experimental Medicine, vol. 20, No. 3, 2002, p. 434-442.
Langer, R., "New Methods of Drug Delivery," *Science*, 249:1527-33 (1990).
Laurent, et al., "The arterial wall: a new pharmacological and therapeutic target," *Fundam. Clin. Pharmacol.*, 10:243-57 (1996).
Leclerc, et al., "Drug prevention of restenosis after angioplasty: an update," Elsevier Science, pp. 722-724 (1995).
Leenaars, et al., "Increased adjuvant efficacy in stimulation of antibody responses after macrophage elimination in vivo," *Immunol.*, 90:337-43 (1997).
Lefkovits, et al., "Pharmacological Approaches for the Prevention of Restenosis After Percutaneous Coronary Intervention," *Progress in Cardiovascular Disease*, 40(2):141-58 (1997).
Lehenkari, et al., "Further Insight into Mechanism of Action of Clodronate: Inhibition of Mitochondrial ADP/ATP Translocase by a Nonhydrolyzable, Adenine-Containing Metabolite," *Mol. Pharmacol.*, 62:1255-1262 (2002).
Li et al., Kinetics of Tumor Necrosis Factor α in plasma and the cardioprotective effect of a monoclonal antibody to tumor necrosis factor α in acute myocardial infarction, 1999, American Heart Journal, vol. 137, No. 6, pp. 1145-1152.
Lodge-Patch, "The Ageing of Cardiac Infarcts, and its Influence on Cardiac Rupture," *Br. Heart J.*, pp. 37-42 (1951).
Luckman, et al., "Nitrogen-Containing Bisphosphonates Inhibit the Mevalonate Pathway and Prevent Post-Translational Prenylation of GTP-Binding Proteins, Including Ras," Journal of Bone and Mineral Research 13:581-589 (Apr. 1998).
Maekawa et al., "Prognostic Significance of Peripheral Monocytosis: After Reperfused Acute Myocardial Infarction: A Possible Role for Left Ventricular Remodeling, 2002, J Am Coll Cardiol, vol. 39, No. 2, pp. 241-246.
Mak, et al., "Clinical Trials to prevent Restenosis after Percutaneous Coronary Revascularization," *The NY Academy of Sciences*, pp. 225-277 (1994).
Makkar, et al., "Prevention of Restenosis by Local Drug Delivery," *J. Cardiovasc. Pharmacol. Therapeut.*, 1(2):177-88 (1996).
Makkonen, et al., "The Effect of Free Gallium & Gallium in Liposomes on Cytokine and Nitric Oxide Secretion from Macrophage-Like Cells in Vitro," Inflamm Res 44:523-528 (1995).
Makkonen, et al., "Contrasting effects of alendronate and clodronate on RAW 264 macrophages: the role of a bisphosphonate metabolite," *Eur. J. Pharm. Sci.*, 8:109-118 (1999).
Makkonen, et al., "Different Effects of Three Bisphosphonates on Nitric Oxide Production by Raw 264 Macrophage-Like Cells in Vitro," *J. Pharmacol. Exp. Ther.*, 277:1097-1102 (1996).
Martin, et al., "Bisphosphonates—mechanisms of action," *Australian Prescriber*, vol. 23, No. 6: 130-132 (2000).
Mateos-Cáreres et al., "Prior Aspirin use in Unstable Angina Patients with Modified Plasma Inflammatory Markers and Endothelial Nitric Oxide Synthase in Neutrophils," European Journal of Clinical Investigation, vol. 32, pp. 895-900 (2002).
Matthews, et al., "Comparison of the response of primary human peripheral blood mononuclear phagocytes from different donors to challenge with model polyethylene particles of known size and dose," *Biomaterials*, 21:2033-44 (2000).
Maximilian et al., "Effect of EHDP on Calcium Accumulation and Technetium-99m Pyrophosphate Uptake in Experimental Myocardial Infarction", Circulation, vol. 64, No. 5, pp. 1012-1017 (1981).
Monkkonen et al., 1995, "Studies on Liposome Formulations for Intra-Articular Delivery of Clodronate," *J. Controlled Release* 35; 145-154.
Monkkonen, et al., "Effects of clodronate and pamidronate on splenic and hepatic phagocytic cells of mice," *Pharmacol. Toxicol.*, 68:284-286 (1991).

(56) References Cited

OTHER PUBLICATIONS

Monkkonen, et al., "Effects of Tiludronate and Ibandronate on the Secretion of Proinflammatory Cytokines and Nitric Oxide from Macrophages in Vitro," *Life Sci.*, 62:PL95-102 (1998).

Monkkonen, et al., "Growth Inhibitions of Macrophage-Like and Other Cell Types by Liposome-Encapsulated, Calcium-Bound, and Free Bisphosphonates In Vitro," *J. Drug Targeting*, 2:299-308 (1994).

Monkkonen, et al., "Liposome-Mediated Delivery of Gallium to Macrophage-Like Cells in Vitro: Demonstration of a Transferrin-Independent Route for Intracellular Delivery of Metal Ions," *Pharm. Res.*, 10(8):1130-1135 (1993).

Monkkonen, et al., "The Cellular Uptake and Metabolism of Clodronate in RAW 264 Macrophages," *Pharm. Res.*, 18:1550-1555 (2001).

Monkkonen, et al., "The effects of liposome surface charge and size on the intracellular delivery of clodronate and gallium in vitro," *Int. J. Pharm.*, 107:189-197 (1994).

Monkkonen, et al., 1993, "The effects of liposome-encapsulated and free clodronate on the growth of macrophage-like cells in vitro: the role of calcium and iron" *Calcif. Tissue Int.* 53:139-146.

Moorman, et al., "Percutaneous Transluminal Coronary Angioplasty (PTCA): Long-term Outcome and Aeromedical Implications," *Aviation, Space and Environmental Medicine*, 67(10):990-6 (1996).

Mullane, et al., "Role of Leukocytes in Acute Myocardial Infarction in Anesthetized Dogs: Relationship to Myocardial Salvage by Anti-inflammatory Drugs," *J. Pharm. Exp. Ther.*, vol. 228(2): 510-522 (1984).

Nandi et al., "Synergistic Effect of PEG-400 and Cyclodextrin to Enhance Solubility of Progesterone," AAPS PharmSciTech. 2003; 4(1): article, 7 pages.

Paspaliaris, et al., "Clodronate Inhibits Contraction and Prevents the Action of L-Type Calcium Channel Antagonists in Vascular Smooth Muscle," *J. Bone Min. Res.*, 6(8):835-841 (1991).

Patashnik et al., 1997, Preparation and evaluation of chitosan microspheres containing bisphosphonates, *J. Drug Targeting* 4:371-380.

Pennanen et al., Effect of Liposomal and Free Bisphosphonates on the IL-1β, IL-6 and TNF-α Secretion from RAW 264 Cells in Vitro, Pharmaceutical Research, vol. 12, No. 6, 1995, pp. 916-922.

Perugini et al., "Long-Term Release of Clodronate from Biodegradable Microspheres," AAPS PharmSciTech. 2001; 2(3): article 10, 11 pages.

Presentation by Inventor Yoram Richter from Examiner Interview submitted Aug. 21, 2008 in prosecution of related U.S. Appl. No. 10/871,488.

Remington's Pharmaceutical Sciences, A.R. Gennaro, ed. Mack Publishing Co. (18th ed. 1990) p. 993.

Rogers, et al., "Monocyte Recruitment and Neointimal Hyperplasia in Rabbits," *Arteriosclerosis, Thrombosis, and Vascular Biology*, 16:1312-18 (1996).

Rosol et al., "Effects of Mithramycin on Calcium Metabolism and Bone in Dogs," Vet Pathology vol. 29, pp. 223-229 (1992).

Rubin, et al., "Cellular and Molecular Mechanisms of Radiation Inhibition of Restenosis. Part I: Role of the Macrophage and Platelet-Derived Growth Factor," *Int. J. Radiation Oncology Biol. Phys.*, 40:929-41 (1998).

Saito et al., "An Investigation of the Stabilization and Regression of Coronary Lesions by Lipid-Lowering Therapy," 66th Annual Scientific Meeting of the Japanese Circulation Society Conference, Japanese Circulation Journal, vol. 10, No. 2, Oct. 2002, p. 233-236.

Sansoni, et al., "Inhibition of antigen-presenting cell function by alendronate in vitro," *J. Bone Min. Res.*, 10(11):1719-25 (1995).

Schroeter, et al., "Phagocytic Response in Photochemically Induced Infarction of Rat Cerebral Cortex," *Stroke*, vol. 28: 382-386 (1997).

Schwarts, "The vessel wall reaction in restenosis," *Semin. Intervent. Cardiol.*, 2:83-8 (1997).

Selander, et al., "Characteristics of the Clodronate-Induced Apoptosis in Osteoclasts and Macrophages," *Mol. Pharmacol.*, 50:1127-1138 (1996).

Shioi, et al., "β-Glycerophosphate Accelerates Calcification in Cultured Bovine Vascular Smooth Muscle Cells," *Arteriosclerosis, Thrombosis and Vascular Biology*, 15(11):2003-9 (1995).

Siiteri, et al., "Immunologic and Endocrine Interrelationships in Pregnancy," *Biol. Reprod.*, vol. 26: 1-14 (1982).

Suresh et al., "In Vitro Activiation of Murine Bone Marrow-Derived Macrophages with Cisplatin and Mitomycin-C," Int. J. Immunopharmacology., vol. 13, Nos. 2/3, pp. 189-195, 1990.

Szebeni, Janos, "The Interactions of Liposomes with the Complement System," *Critical Reviews in Therapeutic Drug Carrier Systems*, 15(1):57-88 (1998).

Takeshita et al., "Drug Action at a Cellular Level," Iryo, The Japanese Journal of the National Medical Services, Mar. 1979, vol. 33, No. 3, pp. 37-39.

Tanaka et al., "Cytotoxic Effects of Selenium on Mouse tsA640-transformed macrophages in vitro," G. Bulletin of Tottori University College of Medical Care Technology, 1992, No. 18, p. 13-20.

Tashiro et al., 1995, "Monocyte-related cytokines in acute myocardial infarction," American Heart Journal 130: 446-452.

Taubes et al., "Does Inflammation Cut to the Heart of the Matter?", Science, vol. 296, No. 5566 pp. 242-245 (2002).

Thepen, et al., "Alveolar macrophage elimination in vivo is associated with an increase in pulmonary immune response in mice," *J. Exp. Med.*, 170:499-509 (1989).

Toyras, et al., "Inhibition of mevalonate pathway is involved in alendronate-induced cell growth inhibition, but not in cytokine secretion from macrophages in vitro," *Eur. J. Pharm. Sci.*, 19:223-230 (2003).

"Unnerving Truth About Diabetic Neuropathy," Diabetes Facts, Diabetes Research, http://www.allaboutdiabetes.net/unnerving-truth-about-diabetic-neuropathy/, Nov. 30, 2008, 5 pages.

Van Lent, et al., "In Vivo Role of Phagocytic Synovial Lining Cells in Onset of Experimental Arthritis," *Am. J. Pathol.*, 143:1226-37 (1993).

Van Offel, et al., "Influence of cyclic intravenous pamidronate on proinflammatory monocytic cytokine profiles and bone density in rheumatoid arthritis treated with low dose prednisolone and methotrexate," *Clin. Exp. Rheum.*, vol. 19: 13-20 (2001).

Van Rooijen et al., "Elimination of Phagocytic Cells in the Spleen after Intravenous Injection of Liposome-Encapsulated Dichloromethylene Diphosphonate: An Enzyme-Histochemical Study" Cell and Tissue Research (1984) 238: pp. 355-358.

Van Rooijen, et al., "Apoptosis of macrophages induced by liposome-mediated intracellular delivery of clodronate and propamidine," *J. Immunol. Methods*, 193:93-9 (1996).

Van Rooijen, et al., "In vitro and in vivo elimination of macrophage tumor cells using liposome-encapsulated dichloromethylene diphosphonate," *Virchows Arch. B* (*Cell Pathol.*), 54:241-245 (1988).

Van Rooijen, et al., "In vivo elimination of macrophages in spleen and liver, using liposome encapsulated drugs: methods and applications," *Liposomes as drug carriers: Trends and progress*, Ed. G. Gregoriadis, John Wiley and Sons, Chichester, U.K. (chapter 9), pp. 131-143 (1988).

Van Rooijen, et al., "Liposome mediated depletion of macrophages: mechanism of action, preparation of liposomes and applications," *J. Immunol. Methods*, 174:83-93 (1994).

Van Rooijen, et al., "Macrophage subset repopulation in the spleen: differential kinetics after liposome-mediated elimination," *J. Leuk. Biol.*, 45:97-104 (1989).

Van Rooijen, et al., "The macrophage as target or obstacle in liposome-based targeting strategies," *Int. J. Pharmaceu.*, 162:45-50 (1998).

Van Rooijen, et al., "Transient suppression of macrophage functions by liposome-encapsulated drugs," *Trends in Biotechnology*, 15(5):178-185 (1997).

Van Rooijen, N., "Liposomes as an in vivo tool to study and manipulate macrophage function: Introduction 41st Forum in Immunology," *Res. Immunol.*, 143:177-178 (1992).

Van Rooijen, N., "Macrophages as accessory cells in the in vivo humoral immune response: from processing of particulate antigens to regulation by suppression," *Semin. Immunol.*, 4:237-245 (1992).

(56) References Cited

OTHER PUBLICATIONS

Viklicky et al., "SDZ-RAD Prevents Manifestation of Chronic Rejection in Rat Renal Allografts," Transplantation, 2000, vol. 69, No. 4, p. 497-502.

Wagner, et al., "Contrasting Effects of Ethane-1-Hydroxy-1, 1-Diphosphonate (EHDP) on the Regression of two types of Dietary-Induced Atherosclerosis," *Atherosclerosis*, 27:419-35 (1977).

Waller, et al., "Coronary Artery and Saphenous Vein Graft Remodeling: A Review of Histologic Findings after Various Interventional Procedure—Part VI," *Clin. Cardiol.*, 20: 153-60 (1997).

Walsh, et al., "Molecular strategies to inhibit restenosis: modulation of the vascular myocyte phenotype," *Semin. Intervent. Cardiol.*, 1:173-9 (1996).

Webb, et al., "Inhibition of Bioprosthetic Heart Valve Calcification with Aminodiphosphonate Covalently Bound to Residual Aldehyde Groups," *Ann. Thorac. Surg.*, 46:309-16 (1988).

Witte, et al., "Delayed and Remote Effects of Focal Cortical Infarctions: Secondary Damage and Reactive Plasticity," *Adv. Neurol.*, vol. 73: 207-227 (1997).

www.clodronateliposomes.com, copyright (c) 1984-2003, download date Sep. 4, 2003.

Ylitalo, 2002, "Bisphosphonates and Atherosclerosis", *General Pharmacology* 35:287-296.

Ylitalo, et al., "Effects of liposome-encapsulated bisphosphonates on acetylated LDL metabolism, lipid accumulation and viability of phagocyting cells," *Life Sciences*, vol. 62, No. 5, pp. 413-422 (1998).

YourDictionary, scientific definition of "heart attack", accessed Jun. 2, 2011 from http://science.yourdictionary.com/heart-attack.

Yue, et al., "In Vivo Myocardial Protection From Ischemia/Reperfusion Injury by the Peroxisome Proliferator-Activated Receptor-γ Agonist Rosiglitazone," *Circulation*, 104:2588-94 (2001).

Office Actions and Response of related U.S. Appl. No. 10/607,623 1 of 2: Final Rejection dated Jun. 22, 2017; Response to Non-Final Rejection with Affidavit and Extension of Time, in response to the Non-Final Rejection dated Mar. 1, 2017; Non-Final Rejection dated Oct. 3, 2016; Amendment and Response to Non-Final Rejection with Request for Continued Exmaination and Extension of Time dated Jul. 22, 2016; Advisory Action dated Jul. 11, 2016; Response to Final Rejection dated Jun. 30, 2016; Final Rejection dated Mar. 3, 2016; Amendment and Response to Non-Final Rejection with Extension of Time dated Nov. 11, 2015; Non-Final Rejection dated Jul. 15, 2015; Amendment and Response to Final Rejection with Request for Continued Examination and Extension of Time dated May 20, 2014; Pre-Brief Appeal Conference Decision dated Jan. 27, 2014; Pre-Appeal Brief Conference Request and Notice of Appeal dated Aug. 19, 2013; Final Rejection dated May 22, 2013; Amendment and Response to Final Rejection with Request for Continued Examination dated Aug. 7, 2012; Final Rejection dated May 10, 2012; Amendment and Response to Non-Final Rejection dated Jan. 30, 2012; Non-Final Rejection dated Oct. 31, 2011; Amendment and Response to Non-Final Rejection dated Jul. 14, 2011; Non-Final Rejection dated Apr. 15, 2011; and Response to Notice of Non-Compliance dated Dec. 8, 2010.

Office Actions and Response of related U.S. Appl. No. 10/607,623 2 of 2: Notice of Non-Compliance Amendment dated Dec. 3, 2010; Amendment and Response to Non-Final Rejection with Extension of Time dated Nov. 29, 2010; Non-Final Rejection dated Aug. 25, 2010; Amendment and Response to Final Rejection with Request for Continued Examination and Extension of Time dated Jun. 30, 2010; Pre-Brief Appeal Conference Decision dated Jun. 1, 2010; Pre-Brief Conference Request and Notice of Appeal dated May 3, 2010; Final Rejection dated Feb. 4, 2010; Examiner Interview Summary dated Nov. 16, 2009; Amendment and Response to Non-Final Rejection with Extension of Time dated Nov. 10, 2009; Non-Final Rejection dated Jun. 11, 2009; Amendment and Response to Final Rejection with Request for Continued Examination dated May 1, 2009; Final Rejection dated Feb. 9, 2009; Examiner Interview Summary dated Jul. 31, 2008; Amendment and Response to Non-Final Rejection with Extension of Time dated Jul. 28, 2008; Examiner Interview Summary dated Jul. 8, 2008; Non-Final Rejection dated Apr. 3, 2008; Amendment and Response to Final Rejection with Request for Continued Examination and Extension of Time dated Jan. 7, 2008; Final Rejection dated Sep. 7, 2007; Amendment and Response to Non-Final Rejection dated May 4, 2007; Non-Final Rejection dated Feb. 8, 2007; Response to the Restriction/Election Requirement dated Jul. 26, 2006; and Requirement for Restriction/Election dated Jun. 28, 2006.

Office Actions and Response of related U.S. Appl. No. 10/871,488, now U.S. Pat. No. 9,498,488: Miscellaneous Communication and Applicant Initiated Interview Summary dated Nov. 1, 2016; Miscellaneous Transmittal Letter and Application Data Sheet in follow-up to Apr. 3, 2006 Request to Correct Inventorship dated Oct. 27, 2016; Issue Fee Payment dated Oct. 13, 2016; Notice of Allowance and Examiner Initiated Interview Summary dated Jul. 13, 2016; Terminal Disclaimer dated Jul. 7, 2016; Terminal Disclaimer Approval dated Jul. 7, 2016; Amendment and Response to Non-Final Rejection dated Jun. 28, 2016; Non-Final Rejection dated Mar. 31, 2016; Amendment and Response to Final Rejection with Request for Continued Examination dated Feb. 25, 2016; Advisory Action dated Feb. 4, 2016; Response and Supplemental Amendment to Final Rejection dated Jan. 25, 2016; Examiner Initiated Interview Summary dated Dec. 30, 2015; Applicant Initiated Interview Summary dated Dec. 21, 2015; Request for Examiner Interview dated Dec. 15, 2015; Final Rejection dated Nov. 25, 2015; Amendment and Response to Non-Final Rejection dated Nov. 10, 2015; Non-Final Rejection dated Aug. 11, 2015; Amendment and Response to Final Rejection with Request for Continued Examination dated Jul. 15, 2015; Applicant Initiated Interview Summary dated Jun. 23, 2015; Final Rejection dated Apr. 17, 2015; Amendment and Response to Non-Final Rejection with Extension of Time dated Apr. 3, 2015; Non-Final Rejection dated Dec. 3, 2014; Amendment and Response to Final rejection with Request for Continued Examination dated May 13, 2014; Applicant Initiated Interview Summary dated Apr. 15, 2014; Final Rejection dated Feb. 20, 2014; Amendment and Response to Non-Final Rejection dated Dec. 16, 2013; Non-Final Rejection dated Sep. 24, 2013; Amendment and Response to Final Rejection with Request for Continued Examination dated Feb. 9, 2012; Applicant Initiated Interview Summary dated Dec. 8, 2011; Final Rejection dated Nov. 20, 2011; Amendment and Response to Non-Final Rejection with Extension of Time dated Aug. 24, 2011; Non-Final Rejection dated Mar. 4, 2011; Amendment and Response to Final Rejection with Request for Continued Examination dated Dec. 22, 2009; Final Rejection dated Oct. 29, 2009; Amendment and Response to Non-Final Rejection dated Jul. 13, 2009; Non-Final Rejection dated Apr. 16, 2009; Amendment and Supplemental Response to Non-Final Rejection dated Jan. 26, 2009; Non-Final Rejection dated Sep. 25, 2008; Response to Final Rejection with Affidavit dated Aug. 21, 2008; Examiner Interview Summary Record dated Jul. 3, 2008; Final Rejection dated May 21, 2008; Amendment and Response to Non-Final Rejection dated Feb. 25, 2008; Non-Final Rejection dated Nov. 26, 2007; and Request to Correct Inventorship dated Apr. 3, 2006.

Issue Fee Payment dated Oct. 13, 2016; Notice of Allowance and Examiner Initiated Interview Summary dated Jul. 13, 2016; Terminal Disclaimer dated Jul. 7, 2016; Terminal Disclaimer Approval dated Jul. 7, 2016; Amendment and Response to Non-Final Rejection dated Jun. 28, 2016; Non-Final Rejection dated Mar. 31, 2016; Amendment and Response to Final Rejection with Request for Continued Examination dated Feb. 25, 2016; Advisory Action dated Feb. 4, 2016; Response and Supplemental Amendemtn to Final Rejection dated Jan. 25, 2016; Examiner Initiated Interview Summary dated Dec. 30, 2015; Applicant Initiated Interview Summary dated Dec. 21, 2015; Request for Examiner Interview dated Dec. 15, 2015; Final Rejection dated Nov. 25, 2015; Amendment and Response to Non-Final Rejection dated Nov. 10, 2015; Non-Final Rejection dated Aug. 11, 2015; Amendment and Response to Final Rejection with Requesr for Continued Examination dated Aug. 15, 2015; Applicant Initiated Interview Summary dated Jun. 23, 2015; Final Rejection dated Apr. 17, 2015; Amendment and Response to Non-Final Rejection with Extension of Time dated Apr. 3, 2015;

(56) References Cited

OTHER PUBLICATIONS

Non-Final Rejection dated Dec. 3, 2014; Amendment and Response to Final rejection with Request for Continued Examination dated May 13, 2014; Applicant Initiated Interview Summary dated Apr. 15, 2014; Final Rejection dated Feb. 20, 2014; Amendment and Response to Non-Final Rejection dated Dec. 16, 2013; Non-Final Rejection dated Sep. 24, 2013; Amendment and Response to Final Rejection with Request for Continued Examination dated Feb. 9, 2012; Applicant Initiated Interview Summary dated Dec. 8, 2011; Final Rejection dated Nov. 20, 2011; Amendment and Response to Non-Final Rejection with Extension of Time dated Aug. 24, 2011; Non-Final Rejection dated Mar. 4, 2011; Amendment and Response to Final Rejection with Request for Continued Examination dated Dec. 22, 2009; Final Rejection dated Oct. 29, 2009; Amendment and Repsonse to Non-Final Rejection dated Jul. 13, 2009; Non-Final Rejection dated Apr. 16, 2009; Amendment and Supplemental Response to Non-Final Rejection dated Jan. 26, 2009; Non-Final Rejection dated Sep. 25, 2008; Response to Final Rejection with Affidavit dated Aug. 21, 2008;.
Office Actions and Response of abandoned U.S. Appl. No. 11/190,787: Notice of Abandonment dated May 31, 2012; Non-Final Rejection dated Nov. 17, 2011; Amendment and Response to Final Rejection with Request for Contintued Examination dated Sep. 9, 2011; Final Rejection dated Jun. 10, 2011; Amendment and Response to Non-Final Rejection dated Jun. 1, 2010; Non-Final Rejection dated Mar. 3, 2010; Examiner Initiated Interview Summary dated Nov. 17, 2009; Amendment and Supplement Response to Non-Final Rejection with Extension of Time dated Nov. 10, 2009; Non-Final Rejection dated Jun. 11, 2009; Amendment and Response to Non-Final Rejection with Extension of Time dated Feb. 25, 2009; Non-Final Rejection dated Oct. 29, 2008; Response to Election/Restriction Requirement dated Aug. 29, 2008; Notice of Non-Compliant Response dated Aug. 26, 2008; Response to Election/Restriction Requirement dated Aug. 21, 2008; and Requirement for Restriction/Election dated Jul. 29, 2008.
Zhao et al., "Myocardial Apoptosis and Ischemic Preconditioning," Cardiovascular Research 55 pp. 438-455 (2002).
Funayama et al., "Plaque and Monocyte/Macrophage," Arteriosclerosis, 26(1): 37-40, 1998.
The Journal of the Japanese Society of Internal Medicine, 1997, vol. 86, No. 6, p. 883-888.
Diada et al., "Acute Coronary Syndrome—Diagnosis and Treatment," The Juntendo Medical Journal, Mar. 28, 2003, vol. 48, No. 4, pp. 448-457.

\* cited by examiner

Control

LA 3 mg/kg

METHOD OF TREATING ACUTE CORONARY SYNDROMES

This application is a continuation of U.S. application Ser. No. 10/871,488 filed Jun. 18, 2004, which is a continuation-in-part of U.S. application Ser. No. 10/607,623 filed Jun. 27, 2003, which is incorporated by reference herein in its entirety.

1. FIELD OF INVENTION

The present invention relates to methods and compositions designed for the treatment or management of acute coronary syndromes, particularly, unstable angina and acute myocardial infarction. The methods of the invention comprise the administration of an effective amount of a formulation containing one or more therapeutic agents which specifically decreases or inhibits the activity of and/or eliminates or diminishes the amount of phagocytic cells including, but not limited to, macrophages and monocytes.

2. BACKGROUND OF THE INVENTION

Coronary artery disease is a leading cause of death in industrialized countries. In the United States, 50-60% of heart attacks occur in people without documented coronary artery disease. A chief contributor to the pathology of the disease is the formation of atherosclerotic plaques. Atherosclerotic plaques are thickened areas in vessel walls which result from an accumulation of cholesterol, proliferating smooth muscle cells, and inflammatory cells.

Atherosclerotic Plaques

In general, an atherosclerotic plaque consists of a raised focal point within the intima having a central core of extra-cellular lipids covered by a fibrous cap. The core within the plaque contains crystalline cholesterol, cholesterol esters, phospholipids, cellular degradation products and collagen remnants. The fibrous cap separates the core of the plaque from the lumen of the blood vessel or artery and is comprised mainly of connective tissues that are a dense, fibrous extracellular matrix made up of collagens, elastins, proteoglycans and other extracellular matrix materials. The fibrous cap varies in thickness, number of smooth muscle cells and macrophages, and collagen content. (Vallabhajosula et al., 1997, *J. Nucl. Med.* 38(11): 1788-1796).

Atherosclerotic plaques can be characterized as active and prone to rupture ("vulnerable or high-risk plaques") or inactive and relatively stable ("stable plaques"). A vulnerable, high-risk or rupture-prone plaque is characterized by an abundance of inflammatory cells (such as macrophages), a thin fibrous cap, and a large lipid core. The size of the lipid pool within the atherosclerotic plaque and the thickness of the overlying fibrous cap are important characteristics predicting the stability of the plaque. The edge of the fibrous cap (the shoulder region) is a location of high stress and predisposed to rupture, in part, due to the accumulation of inflammatory cells (such as macrophages) in the area and their secretion of enzymes that cause degradation of the material that makes up the fibrous cap (Moreno et al, *Circulation.*, 1994, 90:775-8; van der Wal et al., 1994, *Circulation* 89:36-44.; Jander et al, 1998, *Stroke*, 29:1625-1630) which can lead to rupture of the plaque.

Rupture of the lipid-laden plaque exposes the highly thrombogenic core and the sub-endothelial vascular smooth muscle cell component of the arterial wall to circulating blood. Platelet activation, adhesion and aggregation follow this almost immediately. Platelet adhesion and activation results in the release of coagulation factors and the initiation of the coagulation cascade. The released growth factors, specifically platelet-derived growth factor (PDGF) stimulate the proliferation and migration of vascular smooth muscle cells. Proliferation and migration of vascular smooth muscle cells can lead to plaque remodeling and increased vascular stenosis, or interact with the platelets leading to enhanced thrombogenesis (Pasterkamp et al., 2000, *J. Clin. Basic Cardiol.* 3:81-86). The resulting thrombosis caused by the vulnerable plaque can cause unstable angina, acute myocardial infarction, stroke, acute deterioration in peripheral artery disease, or sudden coronary death.

Unstable Angina

The heart requires oxygen-rich blood to function. The right and left coronary arteries branch from the aorta and carry oxygenated blood to the tissues of the heart. When the coronary arteries fail to deliver an adequate amount of oxygen-rich blood (a condition called hypoxia) to the heart, chest pain, pressure, or discomfort, commonly known as angina, result. If this situation is prolonged, oxygen deprivation can damage the heart muscle itself (a situation known as ischemia) either reversibly or irreversibly.

Angina is classified broadly as stable or unstable, depending on its severity and pattern of occurrence. Stable angina occurs when increased physical activity (e.g., hurrying across a street or climbing a long flight of stairs) raises the demand for oxygen-rich blood. Due to a possible multitude of factors (the most common of which is one or more occluded coronary arteries), the supply created by the coronary blood flow cannot meet this increased demand and hypoxia results. Unstable angina is understood as anginal pain that occurs with lesser degrees of exertion, increasing frequency, or at rest (i.e., without exertion). Unstable angina that occurs at rest represents the condition in its most serious form. It usually is caused by the formation of a blood clot in a coronary artery at the site of a ruptured plaque and, if left untreated, it may result in a heart attack and irreversible damage to the heart.

Unstable angina is likely due to the partial rupture of a vulnerable plaque that has become unstable. The plaque's partial rupture causes a thrombus to develop, but does not completely occlude the artery. Endogenous clot-fighting mechanisms serve to break up the clot but, over time, the plaque continues to rupture and the clotting episodes repeat. Although this patient may not have yet suffered a myocardial infarction, he or she is at high risk of doing so (e.g., if the unstable plaque completely ruptures or if the endogenous clot fighting mechanisms cannot eliminate the clot before total occlusion of the artery). Disrupted fibrous caps taken post mortem from patients with unstable angina are often more heavily infiltrated with macrophages at the plaque rupture site than plaque from cases of stable angina.

Acute Myocardial Infarction

Acute myocardial infarction ("AMI") refers to a common clinical condition that leads to necrosis of myocardial tissue. This condition is well known in the art and is characterized by the occurrence of pain (in most cases precordial), characteristic electrocardiographic changes, and an increase in plasma levels of intracellular enzymes (such as creatinine phosphokinase and α-hydroxybutyrate dehydrogenase) or cardiac proteins (such as components of the troponin complex, and myoglobin) released by the necrotic cardiac tissue. AMI may be accompanied by hypotension, circulatory failure, pulmonary edema and arrhythmia. In most cases, but not exclusively, AMI results from vascular injury and thrombosis in the coronary vessels, which causes these vessels to become occluded with subsequent impaired blood flow to the jeopardized myocardium (Fuster et al., 1992, *New Engl. J. Med.*, 326:242-310). In most cases, the time of the occlusion of the coronary vessel can be estimated from the medical history, the course of plasma levels of intracellular heart muscle enzymes and electrocardiographic changes.

The initiating event of many myocardial infarctions (heart attacks) is rupture of an atherosclerotic plaque. Such rupture may result in formation of a thrombus or blood clot in the coronary artery which supplies the infarct zone. The infarct zone or area, as it is commonly referred to, is an area of necrosis which results from an obstruction of blood circulation. The thrombus formed is composed of a combination of fibrin and blood cells. The location, degree and duration of the occlusion caused by the clot determine the mass of the infarct zone and the extent of damage. Ultimately, the extent of myocardial damage caused by the coronary occlusion depends upon the "territory" supplied by the affected vessel, the degree of occlusion of the vessel, the amount of blood supplied by collateral vessels to the affected tissue, and the demand for oxygen of the myocardium whose blood supply has suddenly been limited (Pasternak and Braunwald, 1994, Acute Myocardial Infarction, *Harrison's Principles of Internal Medicine*, 13th Ed., pgs. 1066-77).

Macrophages and the Inflammatory Response

Macrophages are involved in the cause and/or pathology of some coronary syndromes. Macrophage secretion of proteolytic proteins that degrade the fibrous caps of plaques decrease cap thickness as well as increase additional macrophage infiltration thus contributing to plaque instability. Therefore macrophages are considered to have a central role in plaque rupture and their presence in large concentrations is considered predictive to such rupture. Indeed, erosion and/or disruption of the fibrous cap of atherosclerotic plaques is known to modulate arterial thrombus formation, leading to the onset of acute ischemic events. It is clear that rupture at the site of a vulnerable atherosclerotic plaque is the most frequent cause of acute coronary syndromes, such as unstable angina, myocardial infarction or sudden death.

Inflammation has been related both to the pathogenesis of acute myocardial infarctions and to the healing and repair following AMI. Myocardial ischemia prompts an inflammatory response. In addition, reperfusion, the mainstay of current acute therapy of AMI, also enhances inflammation. Reperfusion involves the rapid dissolution of the occluding thrombus and the restoration of blood flow to the area of the heart which has had its blood supply cut off. The presence of inflammatory cells in the ischemic myocardial tissues has traditionally been believed to represent the pathophysiological response to injury. However, experimental studies have shown that while crucial to healing, the influx of inflammatory cells into tissues, specifically macrophages which are phagocytic cells, results in tissue injury beyond that caused by ischemia alone.

Macrophages and other leukocytes infiltrate the myocardium soon after ischemia ensues. Macrophages secrete several cytokines, which stimulate fibroblast proliferation. However, the activated macrophages also secrete cytokines and other mediators that promote myocardial damage. Accordingly, the influx of macrophages into the myocardium increases myocardial necrosis and expands the zone of infarct. Thus, although the acute phase of inflammation is a necessary response for the healing process, persistent activation is in fact harmful to the infarct area as well as the area surrounding it, the so-called 'peri-infarct zone'.

The inflammatory response that follows myocardial ischemia is critical in determining the severity of the resultant damage caused by the activated macrophages. Plasma levels of inflammatory chemotactic factors (macrophage chemoattractant protein-1 (MCP-1), macrophage inflammatory protein-1 alpha (MIP-1 alpha), have been shown to correlate with subsequent heart failure and left ventricular dysfunction (see, for example, Parissis, et al., 2002, *J. Interferon Cytokine Res.*, 22(2):223-9). Peripheral monocytosis (an elevated number of monocytes) at two and three days after AMI is associated with left ventricular dysfunction and left ventricular aneurysm, suggesting a possible role of monocytes in the development of left ventricular remodeling after reperfused AMI (Maekawa, Y. et al., 2002, *J. Am. Coll. Cardiol.*, 39(2):241-6). Left ventricular remodeling after acute myocardial infarction is the process of infarct expansions followed by progressive left ventricular dilation and is associated with an adverse clinical outcome. Furthermore, plasma levels of macrophage chemoattractant protein-1 (MCP-1) are elevated in patients with acute myocardial infarction. MCP-1 is induced by myocardial ischemia/reperfusion injury and neutralization of this chemokine significantly reduced infarct size.

Suppression of the inflammatory response by nonspecific anti-inflammatory composites after coronary occlusion, in several coronary occlusion/reperfusion models, was shown to reduce the infarct area (See, for example, Squadrito, et al., 1997, *Eur. J. Pharmacol.*; 335:185-92; Libby, et al., 1973, *J. Clin. Invest.*, 3:599-607; Spath, et al., 1974, *Circ. Res.*, 35: 44-51). However, these nonspecific regimens are associated with adverse effects, such as interference with scar formation and healing, and, in some patients, the development of aneurysm and rupture of the ventricular wall. As such, these regimens are precluded from clinical use. However, animal models that have a decreased ability to suppress macrophage function due to a deficiency in the anti-inflammatory cytokine interleukin-10 were shown to suffer from increased infarct size and myocardial necrosis in a coronary occlusion model (Yang, Z. et al., 2000, *Circulation*, 101:1019-1026.)

One object of the present invention is the identification of therapeutic agents capable of blocking the accumulation of and/or the biological function including secretion of factors from phagocytic cells (particularly macrophages and monocytes) in the patient suffering from an acute coronary syndrome (particularly unstable angina or and acute myocardial infarction).

Another object of the invention is the development of methods for treating an acute coronary syndrome (particularly unstable angina or and acute myocardial infarction) as well as stabilizing the plaques associated with these syndromes.

3. SUMMARY OF THE INVENTION

The present invention relates to methods and compositions designed for the treatment or management of acute coronary syndromes, particularly, unstable angina and acute myocardial infarction. The methods of the invention comprise the administration of an effective amount of a formulation containing one or more therapeutic agents which specifically inhibits the activity of and/or diminishes the amount of phagocytic cells including, but not limited to, macrophages and monocytes. Administration of a formulation containing one or more therapeutic agents according to the invention acts as an acute, treatment aimed at stabilizing the patient's coronary syndrome condition. In one embodiment, a formulation containing one or more therapeutic agents is administered to a patient suffering from unstable angina to stabilize a vulnerable or unstable plaque. In another embodiment, a formulation is administered to a patient currently suffering or recently having suffered an acute myocardial infarction to minimize infarct size and myocardial necrosis.

In preferred embodiments, the formulation specifically targets phagocytic cells. Because phagocytic cells possess the unique ability of phagocytosis, in these embodiments, the formulations are prepared such that they comprise particles of such properties as to enter into a cell primarily or exclusively via phagocytosis. The formulation may comprise an encapsulated therapeutic agent, an embedded therapeutic agent, or a particulate therapeutic agent. Once phagocytosed, the therapeutic agent is released from the formulation into the targeted phagocytic cells, e.g., macrophages and monocytes, and inhibits the function of and/or destroys the phagocytic cell.

In one embodiment, the present invention relates to a method of treating an acute coronary syndrome by administering to an individual in need thereof an effective amount of a formulation comprising an encapsulated therapeutic agent. The therapeutic agent is encapsulated in a suitable carrier of a specific dimension. The formulation specifically targets phagocytic cells by virtue of its properties, such as, for example, size or charge, which allow the formulation to be taken-up primarily or exclusively by phagocytosis. Once the formulation is taken-up by the phagocytic cell, the encapsulated therapeutic agent is released and the agent is able to inhibit the activity of and/or destroy the phagocytic cell.

In another embodiment, the present invention relates to a method of treating an acute coronary syndrome by administering to an individual in need thereof an effective amount of a formulation comprising an embedded therapeutic agent. The therapeutic agent is embedded in a suitable carrier of a specific dimension. The formulation specifically targets phagocytic cells by virtue of its properties, such as, for example, size and/or charge, which allow the formulation to be taken-up primarily or exclusively by phagocytosis. Once inside the phagocytic cells the embedded therapeutic agent is released and the agent is able to inhibit the activity of and/or destroy the phagocytic cell.

In another embodiment, the present invention relates to a method of treating an acute coronary syndrome by administering to an individual in need thereof an effective amount of a formulation comprising a particulate therapeutic agent. The therapeutic agent is made into particulates of a specific dimension. The formulation specifically targets phagocytic cells by virtue of the particulate's properties, such as, for example, size and/or charge, which allow the formulation to be taken-up primarily or exclusively by phagocytosis. Once inside the phagocytic cells the particulate therapeutic agent is able to inhibit the activity of and/or destroy the phagocytic cell.

The present invention also relates to a method of stabilizing plaques associated with an acute coronary syndrome by administering to an individual in need thereof an effective amount of a formulation comprising an encapsulated, embedded, or particulate therapeutic agent.

In a further embodiment, the present invention includes a pharmaceutical composition for administration to subjects currently suffering from or having recently suffered an acute coronary syndrome such as unstable angina and acute myocardial infarction comprising a formulation selected from the group consisting of an encapsulated therapeutic agent, an embedded therapeutic agent, and a particulate therapeutic agent together with a pharmaceutically acceptable vehicle, carrier, stabilizer or diluent for the treatment of an acute coronary syndrome.

The formulation of present invention is preferably in the size range of 0.03-1.0 microns. However, depending on the type of agent and/or the carrier used, the more preferred ranges include, but are not limited to, 0.07-0.5 microns, 0.1-0.3 microns and 0.1 to 0.18.

4. BRIEF DESCRIPTION OF THE FIGURES

FIG. 1 illustrates the effect of liposomal alendronate treatment on the size of infarct area after transient coronary artery occlusion in rabbits. The size of the infarct zone was calculated as the area of the infarcted zone as a % of the left ventricular area supplied by the occluded artery and thus at risk for subsequent infarction. Data are expressed as mean±SD, with n=4/group and a p value of $p<0.05$.

5. DETAILED DESCRIPTION OF THE INVENTION

Figure 1:
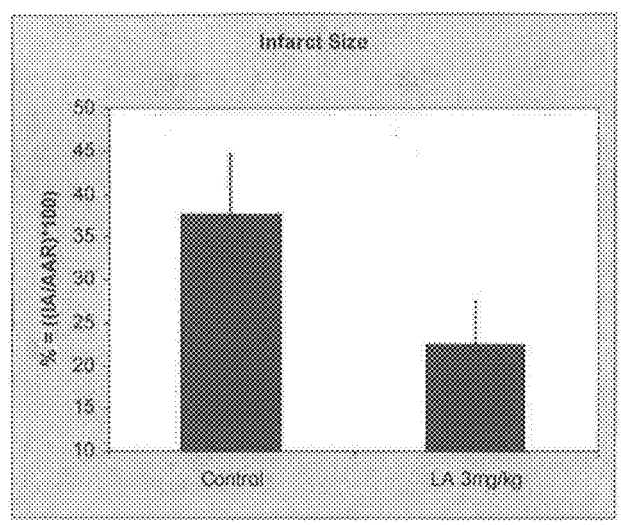

Phagocytic cells, particularly macrophages and monocytes, are involved in the cause and/or pathology of some coronary syndromes. Macrophages/monocytes degrade the fibrous caps of plaques through the secretion of various substances that not only decrease cap thickness, but also serve to recruit additional macrophages/monocytes to the area. Degradation of the fibrous cap leads to exposure to blood of the lipid core of the plaque as well as initiation of the clotting cascade which culminates in a thrombus. The thrombus may partially occlude the lumen leading to unstable angina or it may completely occlude the lumen thus causing an acute myocardial infarction. Once an acute myocardial infarction occurs, macrophages/monocytes are recruited to the damaged myocardial tissue and secrete cytokines and other mediators that promote myocardial damage thus resulting in tissue injury beyond that caused by ischemia alone and increases myocardial necrosis which expands the zone of infarct. Although a complete and chronic incapacitation and/or ablation of phagocytic cells is not desirable, such a decrease in phagocytic cell activity and/or presence is desirable in the short term during or after an acute coronary syndrome to stabilize the patient and/or reduce the damage of the coronary syndrome.

The present invention relates to methods and compositions designed to decrease or inhibit the activity of and/or eliminate or diminish the amount of phagocytic cells (including, but not limited to, macrophages and monocytes) for an acute, short term period during or following an acute coronary syndrome for the treatment or management of the acute coronary syndrome (including, but not limited to, unstable angina and acute myocardial infarction). The methods of the invention comprise the administration of an effective amount of a formulation containing one or more therapeutic agents which specifically decreases or inhibits the activity of and/or eliminates or diminishes the amount of phagocytic cells (including, but not limited to, macrophages and monocytes) in a patient. Administration of a formulation containing one or more therapeutic agents is contemplated as an acute, short term treatment aimed at stabilization of the patient and/or minimization of the immediate and long term damage from the acute coronary syndrome. In one embodiment, a formulation containing one or more therapeutic agents are administered to a patient suffering from unstable angina to stabilize a vulnerable or unstable plaque and decrease the immediate threat of an acute myocardial infarction. In another embodiment, one or more therapeutic agents are administered to a patient currently suffering or recently having suffered an acute myocardial infarction to minimize the infarct size and myocardial necrosis.

The formulations used in the methods of the invention specifically decrease or inhibit the activity of phagocytic cells and/or eliminate or diminish the amount of phagocytic cells in a patient. Specificity of the formulation is due to the ability of the composition to affect only particular cell types (e.g., macrophages and/or monocytes). In preferred embodiments, specificity of the formulation for phagocytic cells is due to the physiochemical properties, e.g. size or charge, of the formulation such that it can only or primarily be internalized by phagocytosis. Once phagocytosed and intracellular, the therapeutic agent inhibits or decreases the activity of the phagocytic cell and/or destroys the phagocytic cell. Although not intending to be bound by any particular mechanism of action, the therapeutic agents of the formulation are released upon becoming intracellular before disabling an/or destroying the phagocytic cell.

The formulation of the present invention, e.g., the encapsulated therapeutic agent, embedded therapeutic agent or the particulate therapeutic agent, suppresses the inflammatory response by transiently depleting and/or inactivating cells that are important triggers in the inflammatory response, namely macrophages and/or monocytes. The encapsulated agent, embedded agent and/or particulate agent are taken-up, by way of phagocytosis, by the macrophages and monocytes. In contrast, non-phagocytic cells are incapable of taking up the formulation due to the large dimension and/or other physiochemical properties of the formulation.

The term "phagocytosis" as used herein refers to a preferred means of entry into a phagocytic cell and is well understood in the art. However, the term should be understood to also encompass other forms of endocytosis which may also accomplish the same effect. In particular, it is understood that pinocytosis, receptor-mediated endocytosis and other cellular means for absorbing/internalizing material from outside the cell are also encompassed by the methods and compositions of the present invention.

The invention also provides pharmaceutical compositions comprising one or more therapeutic agents of the invention for administration to subjects currently suffering from or recently having suffered an acute coronary syndrome such as unstable angina and acute myocardial infarction.

5.1 Therapeutic Agents

The therapeutic agents used in the formulations and in the methods of the invention specifically decrease or inhibit the activity of phagocytic cells and/or eliminate or diminish the amount of phagocytic cells in a patient, by virtue of the physiochemical properties, such as size or charge, of the formulation. The therapeutic agent may be an intracellular inhibitor, deactivator, toxin, arresting substance and/or cytostatic/cytotoxic substance that, once inside a phagocytic cell such as a macrophage or monocyte, inhibits, destroys, arrests, modifies and/or alters the phagocytic cell such that it can no longer function normally and/or survive.

As used herein, the term "therapeutic agents" refers to molecules which either make up the formulation or form a part of the formulation and provide the inactivating/toxic potency to the formulation, e.g., inhibits or decreases phagocytic cell activity and/or eliminates or decreases the amount of phagocytic cells. Compounds that can be therapeutic agents include, but are not limited to, inorganic or organic compounds; or a small molecule (less than 500 daltons) or a large molecule, including, but not limited to, inorganic or organic compounds; proteinaceous molecules, including, but not limited to, peptide, polypeptide, protein, post-translationally modified protein, antibodies etc.; or a nucleic acid molecule, including, but not limited to, double-stranded DNA, single-stranded DNA, double-stranded RNA, single-stranded RNA, or triple helix nucleic acid molecules. Compounds can be natural products derived from any known organism (including, but not limited to, animals, plants, bacteria, fungi, protista, or viruses) or from a library of synthetic molecules. Therapeutic agents can be monomeric as well as polymeric compounds.

In preferred embodiments where the preferred therapeutic agent may be a bisphosphonate or analog thereof. The term "bisphosphonate" as used herein, denotes both geminal and non-geminal bisphosphonates. In a specific embodiment, the bisphosphonate has the following formula (I):

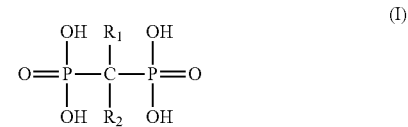

(I)

wherein $R_1$ is H, OH or a halogen atom; and $R_2$ is halogen; linear or branched $C_1$-$C_{10}$ alkyl or $C_2$-$C_{10}$ alkenyl optionally substituted by heteroaryl or heterocyclyl $C_1$-$C_{10}$ alkylamino or $C_3$-$C_8$ cycloalkylamino where the amino may be a primary, secondary or tertiary; —NHY where Y is hydrogen, $C_3$-$C_8$ cycloalkyl, aryl or heteroaryl; or $R_2$ is —SZ where Z is chlorosubstituted phenyl or pyridinyl.

In a more specific embodiment, the bisphosphoate is alendronate or an analog thereof. In such an embodiment, the alendronate has the following formula (II):

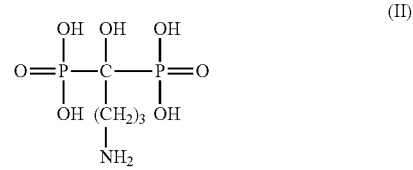

(II)

In other specific embodiments, additional bisphosphonates can be used in the methods of the invention. Examples of other bisphosphonates include, but are not limited to, clodronate, tiludronate, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3(methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-pentylamino)-1-hydroxypropane-1,1-diphosphonic acid, e.g. methyl-pentyl-APD; 1-hydroxy-2-

(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydroxypropane-1,1-bisphosphonic acid; 1-hydroxy-3-(pyrrolidin-1-yl)propane-1,1-bisphosphonic acid, 1-(N-phenylaminothiocarbonyl) methane-1,1-diphosphonic acid, e.g. FR 78844 (Fujisawa); 5-benzoyl-3,4-dihydro-2H-pyrazole-3,3-diphosphonic acid tetraethyl ester, e.g. U81581 (Upjohn); and 1-hydroxy-2-(imidazo[1,2-a]pyridin-3-yl)ethane-1,1-diphosphonic acid, e.g. YM 529, or analogs thereof.

Other formulations containing therapeutic agents include, but are not limited to, gallium, gold, selenium, gadolinium, silica, mithramycin, paclitaxel, sirolimus, everolimus, and other similar analogs thereof. Generally, chemotherapeutic agents, such as, for example, 5-fluorouracil, cisplatinum, alkylating agents and other anti-proliferation or anti-inflammatory compounds, such as, for example, steroids, aspirin and non-steroidal anti-inflammatory drugs may also be used in a formulation.

The present invention is meant to encompass the administration of one or more formulations to manage or treat an acute coronary syndrome. More than one formulation can be administered in combination to the patient. The term "in combination" is not limited to the administration of the formulation at exactly the same time, but rather it is meant that the formulations are administered to a patient in a sequence and within a time interval such that they can act together to provide an increased benefit than if they were administered otherwise. For example, each formulation may be administered at the same time or sequentially in any order at different points in time; however, if not administered at the same time, they should be administered sufficiently close in time so as to provide the desired therapeutic effect. Each formulation can be administered separately, in any appropriate form and by any suitable route which effectively transports the therapeutic agent to the appropriate or desirable site of action. Preferred modes of administration include intravenous (IV) and intra-arterial (IA). Other suitable modes of administration include intramuscular (IM), subcutaneous (SC), and intraperitoneal (IP) and oral (PO). Such administration may be bolus injections or infusions. Another mode of administration may be by perivascular delivery. The formulation may be administered directly or after dilution. Combinations of any of the above routes of administration may also be used in accordance with the invention.

In various embodiments, the formulations are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In one embodiment two or more formulations are administered concurrently or within the same patient visit.

5.1.1 Identification of Therapeutic Agents

The invention provides methods of screening for compounds that can be used as a therapeutic agent. Although not intending to be bound by a particular mechanism of action, a compound that is a therapeutic agent for use in the methods of the invention can, once targeted to the phagocytic cell by the physiochemical properties of the formulation itself, i) inhibit phagocytic cell activity, ii) decrease phagocytic cell activity, iii) eliminate phagocytic cells from circulation and/or from the area affected by the acute coronary syndrome, and/or iv) decrease the number of phagocytic cells in circulation and/or in the area affected by the acute coronary syndrome.

The methods of screening for therapeutic agents generally involve incubating a candidate compound with phagocytic cells either in vitro or in vivo and then assaying for an alteration (e.g., decrease) in phagocytic cell activity or longevity thereby identifying a compound that is a therapeutic agent for use in the present invention. Any method known in the art can be used to assay phagocytic cell activity or longevity. In one embodiment, phagocytic cell activity is assayed by the level of cell activation in response to an activating stimulus. For example, macrophage/monocyte activation can be assayed by quantifying the levels of chemotactic factors such as macrophage chemoattractant protein-1 (MCP-1) and macrophage inflammatory protein-1 alpha (MIP-1 alpha) as well as other substances produced by macrophages such as interleukin 1 beta (IL-1$\beta$) and tissue necrosis factor alpha (TNF-$\alpha$). In another embodiment, phagocytic cell longevity is assayed. For example, cell proliferation can be assayed by measuring $^3$H-thymidine incorporation, by direct cell count, by detecting changes in transcriptional activity of known genes such as proto-oncogenes (e.g., fos, myc) or cell cycle markers; or by trypan blue staining. Any method known in the art can be used to assay for levels of mRNA transcripts (e.g., by northern blots, RT-PCR, Q-PCR, etc.) or protein levels (e.g., ELISA, western blots, etc.).

In one embodiment, a compound that decreases the activity of a phagocytic cell is identified by:

a) contacting a phagocytic cell with a first compound and a second compound, said first compound being a compound which activates said phagocytic cell and said second compound being a candidate compound; and b) determining the level of activation in said contacted phagocytic cell, wherein a decrease in activation in said contacted cell as compared to the level of activation in a phagocytic cell contacted with said first compound in the absence of said second (i.e., a control cell) indicates that said second compound decreases the activity of a phagocytic cell.

In another embodiment, a compound that decreases the amount of phagocytic cells is identified by:

a) contacting a phagocytic cell with a compound; and b) determining the viability of said contacted phagocytic cell, wherein a decrease in viability in said contacted cell as compared to the viability of a phagocytic cell not contacted with said compound (i.e., a control cell) indicates that said compound decreases the amount of phagocytic cells.

In other embodiments, candidate compounds are assayed for their ability to alter phagocytic cell activity or longevity in a manner that is substantially similar to or better than compounds known to alter phagocytic cell activity or longevity in a therapeutically desirable way. As used herein "substantially similar to" refers to an agent having similar action on a phagocytic cell as an exemplified agent, i.e., an agent that inhibits the activity, function, motility, and/or depletion of phagocytic cells.

Additionally, candidate compounds can be used in animal models of acute coronary syndromes to assess their ability to be used in the methods of the invention. In one embodiment, a rabbit AMI model can be used (see e.g., Section 6.1).

5.2 Formulation of Therapeutic Agents

Formulations containing one or more therapeutic agents can be prepared so that the size of the formulation is large enough to only or primarily be internalized by phagocytosis, thus imparting specificity to phagocytic cells. Although non-phagocytic cells may be affected by such a formulation should it become intracellular, there is no mechanism for a non-phagocytic cell to internalize a formulation prepared in this manner. Formulations imparting extrinsic specificity to one or more therapeutic agents are preferably in the size range of 0.03-1.0 microns, more preferably 0.07-0.5 microns, more preferably 0.1-0.3 microns, and more preferably 0.1 to 0.18 microns.

Any method known in the art can be used to incorporate a therapeutic agent into a formulation such that it can only or primarily be internalized via phagocytosis. Formulations of therapeutic agents may sequester the therapeutic agents for a sufficient time to enhance delivery of the agent to the target site. Furthermore, formulations of therapeutic agents may discharge the therapeutic agent from the particles when they are within the target cell (e.g., the phagocytic cell) at the target site.

In one embodiment, the therapeutic agent is encapsulated in a carrier (i.e., encapsulating agent) of desired properties. In a specific embodiment, the encapsulating agent is a liposome. The liposomes may be prepared by any of the methods known in the art (see, e.g., Mönkkönen, J. et al., 1994, *J. Drug Target*, 2:299-308; Mönkkönen, J. et al., 1993, *Calcif. Tissue Int.*, 53:139-145; Lasic D D., Liposomes Technology Inc., Elsevier, 1993, 63-105. (chapter 3); Winterhalter M, Lasic D D, *Chem Phys Lipids*, 1993 September; 64(1-3):35-43). The liposomes may be positively charged, neutral or, more preferably, negatively charged. The liposomes may be a single lipid layer or may be multilamellar. Suitable liposomes in accordance with the invention are preferably non-toxic liposomes such as, for example, those prepared from phosphatidyl-choline phosphoglycerol, and cholesterol. The diameter of the liposomes used preferably ranges from 0.03-1.0 μm. However, other size ranges suitable for phagocytosis by phagocytic cells may also be used.

In another embodiment, the therapeutic agent is embedded in a carrier (i.e., embedding agent) of desired properties. A therapeutic agent which is embedded includes those therapeutic agents that are embedded, enclosed, and/or adsorbed within a carrier, dispersed in the carrier matrix, adsorbed or linked on the carrier surface, or a combination of any of these forms. In specific embodiments, the embedding agent (or carrier) is a microparticle, nanoparticle, nanosphere, microsphere, microcapsule, or nanocapsule (see e.g., M. Donbrow in: *Microencapsulation and Nanoparticles in Medicine and Pharmacy*, CRC Press, Boca Raton, Fla., 347, 1991). The term carrier includes both polymeric and non-polymeric preparations. In a specific embodiment, the embedding agent is a nanoparticle. Preferably, nanoparticles are 0.03-1.0 microns in diameter and can be spherical, non-spherical, or polymeric particles. The therapeutic agent may be embedded in the nanoparticle, dispersed uniformly or non-uniformly in the polymer matrix, adsorbed on the surface, or in combination of any of these forms. In a preferred embodiment, the polymer used for fabricating nanoparticles is biocompatible and biodegradable, such as poly(DL-lactide-co-glycolide) polymer (PLGA). However, additional polymers which may be used for fabricating the nanoparticles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like.

In another embodiment, the therapeutic agent is in particulate form, the particles each being of desired properties. A particulate therapeutic agent form includes any insoluble suspended or dispersed particulate form of the therapeutic agent which is not encapsulated, entrapped or absorbed within a carrier. A therapeutic agent which is in particulate form includes those therapeutic agents that are suspended or dispersed colloids, aggregates, flocculates, insoluble salts, insoluble complexes, and polymeric chains of an agent. Such particulates are insoluble in the fluid in which they are stored/administered (e.g., saline or water) as well as the fluid in which they provide their therapeutic effect (e.g., blood or serum). Typically, "insoluble" refers to a solubility of one (1) part of a particulate therapeutic agent in more than ten-thousand (10,000) parts of a solvent. Any method known in the art to make particulates or aggregates can be used. Preferably, particulates are 0.03-1.0 microns in diameter and can be any particular shape.

5.2.1 Determination of Particle Size

Formulations containing therapeutic agents are preferably prepared such that the size of the formulation is large enough to only or primarily be internalized by phagocytosis, that is, preferably larger than 0.03 microns. In preferred embodiments, such formulations are 0.03-1.0 microns, more preferably 0.07-0.5 microns, more preferably 0.1-0.3 microns, and most preferably 0.1 to 0.18 microns. Any method known in the art can be used to determine the size of the formulation before administration to a patient in need thereof. For example, a Nicomp Submicron Particle Sizer (model 370, Nicomp, Santa Barbara, Calif.) utilizing laser light scattering can be used.

5.3 Administration of the Formulation

Effective amounts of the formulations are contemplated as short term, acute therapy and are not meant for chronic administration. Time period of treatment is preferably such that it produces inhibition/depletion of phagocytic cells for a period that is less than a month, preferably less than two weeks, most preferably up to one week. Empirically, one can determine this by administering the compound to an individual in need thereof (or an animal model of such an individual) and monitoring the level of inhibition/depletion at different time points. One may also correlate the time of inhibition with the appropriate desired clinical effect, e.g. reduction in the acute risk of plaque rupture.

5.4 Characterization of Therapeutic Utility

The term "effective amount" denotes an amount of a particular formulation which is effective in achieving the desired therapeutic result, namely inhibited or decreased phagocytic cell activity and/or elimination or reduction in the amount of phagocytic cells. In one embodiment, the desired therapeutic result of inhibiting or decreasing phagocytic cell activity and/or eliminating or reducing in the amount of phagocytic cells stabilizes a vulnerable or unstable plaque in a patient suffering from unstable angina. In another embodiment, the desired therapeutic result of inhibiting or decreasing phagocytic cell activity and/or eliminating or reducing in the amount of phagocytic cells minimizes the infarct size and/or the amount of myocardial necrosis in a patient having suffered an acute myocardial infarction.

Toxicity and efficacy of the therapeutic methods of the instant invention can be determined by standard pharmaceutical procedures in cell cultures or experimental animals, e.g., for determining the $LD_{50}$ (the dose lethal to 50% of the population), the No Observable Adverse Effect Level (NOAEL) and the $ED_{50}$ (the dose therapeutically effective in 50% of the population). The dose ratio between toxic and therapeutic effects is the therapeutic index and it can be expressed as the ratio $LD_{50}/ED_{50}$ or $NOAEL/ED_{50}$. Formulations that exhibit large therapeutic indices are preferred. While formulations that exhibit toxic side effects may be used, care should be taken to design a delivery system that targets the agents of such formulations to the site of affected tissue in order to minimize potential damage to unaffected cells and, thereby, reduce side effects.

The data obtained from the cell culture assays and animal studies can be used in determining a range of dosage of the formulation for use in humans. The dosage of such formulations lies preferably within a range of circulating concentrations that include the $ED_{50}$ with little or no toxicity. The dosage may vary within this range depending upon the dosage form employed and the route of administration utilized. For any formulation used in the method of the invention, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The protocols and compositions of the invention are preferably tested in vitro, and then in vivo, for the desired therapeutic activity, prior to use in humans. One example, of such an in vitro assay is an in vitro cell culture assay in phagocytic cells which are grown in culture, and exposed to or otherwise administered to cells, and observed for an effect of this assay upon the cells, e.g., inhibited or decreased activity and/or complete or partial cell death. The phagocytic cells may be obtained from an established cell line or recently isolated from an individual as a primary cell line. Many assays standard in the art can be used to measure the activity of the formulation on the phagocytic cells; for example, macrophage/monocyte activation can be assayed by quantitating the levels of chemotactic factors such as macrophage chemoattractant protein-1 (MCP-1), interleukin 1 beta (IL-1β), tissue necrosis factor alpha (TNF-α) and macrophage inflammatory protein-1 alpha (MIP-1 alpha). Many assays standard in the art can be used to assess survival and/or growth of the phagocytic cells; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining.

Selection of the preferred effective dose can be determined (e.g., via clinical trials) by a skilled artisan based upon the consideration of several factors known to one of ordinary skill in the art. Such factors include the acute coronary syndrome to be managed or treated, the symptoms involved, the patient's body mass, the patient's immune status and other factors known to the skilled artisan to reflect the accuracy of administered pharmaceutical compositions.

5.5 Pharmaceutical Compositions and Routes of Administration

Formulations comprising one or more therapeutic agents for use in the methods of the invention may be in numerous forms, depending on the various factors specific for each patient (e.g., the severity and type of disorder, age, body weight, response, and the past medical history of the patient), the number and type of therapeutic agents in the formulation, the type of formulation (e.g., encapsulated, embedded, particulate, etc.), the form of the composition (e.g., in liquid, semi-liquid or solid form), and/or the route of administration (e.g., oral, intravenous, intramuscular, intra-arterial, intramedullary, intrathecal, intraventricular, transdermal, subcutaneous, intraperitoneal, intranasal, enteral, topical, sublingual, vaginal, or rectal means). Pharmaceutical carriers, vehicles, excipients, or diluents may be included in the compositions of the invention including, but not limited to, water, saline solutions, buffered saline solutions, oils (e.g., petroleum, animal, vegetable or synthetic oils), starch, glucose, lactose, sucrose, gelatin, malt, rice, flour, chalk, silica gel, sodium stearate, glycerol monostearate, talc, sodium chloride, dried skim milk, glycerol, propylene, glycol, ethanol, dextrose and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms.

Pharmaceutical compositions can be administered systemically or locally, e.g., near the site of pathology of an acute coronary syndrome. Additionally, systemic administration is meant to encompass administration that can target to a particular area or tissue type of interest.

Pharmaceutical compositions are preferably administered immediately at the onset of the first symptoms of actual plaque rupture; such as, for example, chest pain, pain that radiates to the shoulder, arm, teeth, jaw, abdomen or back or shortness of breath or cough, lightheadedness, fainting, nausea, vomiting, sweating or anxiety associated with a plaque rupture. Other symptoms will be apparent to the skilled artisan and medical doctor, and may be signals to administer the instant pharmaceutical composition. Alternatively and/or additionally, the pharmaceutical compositions may be administered just after onset of symptoms, for example, within minutes of symptom onset. Alternatively and/or additionally, the compositions may be administered within 1 hour, or about 2 hours, or about 3 hours or about 4 hours, or about 5 hours or about 6 hours, up to within 1-3 days after onset of symptoms.

In another regime, pharmaceutical compositions are administered to a patient with an increased risk of plaque rupture. For example, the compositions of the invention may be administered to a patient prior to a procedure which increases the risk of plaque rupture, such as, for example, an angioplasty procedure. It may be preferred to administer the composition up to 3 days before such a procedure. Also preferred, administration may be 1-6 hours before the procedure or within 1 hour of the procedure or less than 1 hour before or even within minutes of the procedure. The skilled person can readily determine the appropriate timing of administration depending on various physiological factors, specific to the individual patient, such as, for example, weight, medical history and genetic predisposition, as well as various factors which influence the anticipated risk of plaque rupture such as complexity of the procedure to be performed.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

6. EXAMPLES

The following examples as set forth herein are meant to illustrate and exemplify the various aspects of carrying out the present invention and are not intended to limit the invention in any way.

6.1 Effect of Liposomal Alendronate on the Size of the Zone of Infarct

The effects of treatment with encapsulated bisphosphonates on the zone of infarct were studied in a rabbit AMI model. Liposomal Alendronate, approx. 0.150 μm in diameter was made using the following outline:
a. Dissolve lipids, DSPC, DSPG and cholesterol in 1/1 ethanol/tert-butanol.
b. Dilute solvent into buffer containing Alendronate to generate large multilamellar vesicles (MLVs).
c. Extrude MLVs through 200 nm polycarbonate filters to generate large unilamellar 150±20 nm vesicles (LUVs).
d. Ultra-filtrate LUVs to remove un-encapsulated alendronate.
e. Sterile filter Eight New Zealand White male rabbits, 2.5-3.5 kg B.W., were fed normal chow and water ad libitum. The rabbits were randomly adminstered saline (control) or liposomal alendronate (3 mg/kg, i.v.) as a single infusion simultaneous with coronary artery occlusion. The rabbits were anesthetized by Ketamine/Xylazine (35 mg/kg; 5 mg/kg) and Isoflurane. The experiment was performed with respiratory support given by intubation and mechanical ventilation with isoflurane in balance oxygen, and continuous echocardiogram (ECG) and arterial blood pressure (catheter in ear artery) monitoring. Thoracotomy was performed through the left $4^{th}$ intercostal space, followed by pericardiotomy and creation of a pericardial cradle. The left main coronary artery was identified and a large branch was encircled by a 5-0 silk suture and a snare. Thereafter, the snare was tightened for 30 minutes. Ischemia was verified by ECG changes (ST-T segment elevation), changes of segment coloration and hypokinesia. After thirty minutes, the snare was released and resumption of blood flow was confirmed. The suture was left in place, released, and the chest cavity was closed in layers. Buprenex was administered to the rabbits for analgesia for 2-3 additional days. Following euthanasia with Penthotal, the rabbits were sacrificed after 7 days and the hearts were harvested. The coronary arteries were perfused through the ascending aorta with saline, followed by tightening of the suture on the previously occluded coronary artery and perfusion of the coronary arteries with 0.5% Evans blue solution (Sigma) to stain areas of re-endothelialization (presence of blood). The left ventricular area unstained by Evans blue was defined as the area at risk. The hearts were then frozen at −20° C. for 24 hours and cut into transverse sections 2 mm apart. Slices of the hearts were incubated for 30 minutes in the vital stain tritetrazolium chloride (TTC, 1%, Sigma), fixed in 10% natural buffered formalin to stain cells that had been alive previous to tissue processing. The left ventricular area not stained by TTC (white) was defined as the area of infarct. The stained sections were then photographed and processed by digital planimetry (Photoshop).

Rabbits treated with liposomal alendronate had a zone of infarct that was 29.5±6% of the area at risk. This was contrasted with the control rabbits (untreated with liposomal alendronate) which showed an infarct zone that was 42±5.5% of the area at risk (FIG. 1). Accordingly, liposomal alendronate was effective in reducing the zone of infarct. No adverse effects were observed in the treatment group.

6.2 Effect of Liposomal Alendronate on Myocardial Morphology

Figure 2A:
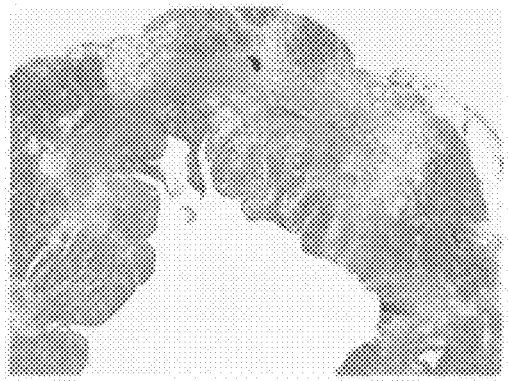
FIGS. 2A-2B illustrate the effect of liposomal alendronate treatment on myocardial morphology after reversible coronary occlusion in rabbits. Control rabbits (A) have distorted myocardial morphology while rabbits treated with liposomal alendronate (B) have a more normal myocardial morphology.
Figure 2B:
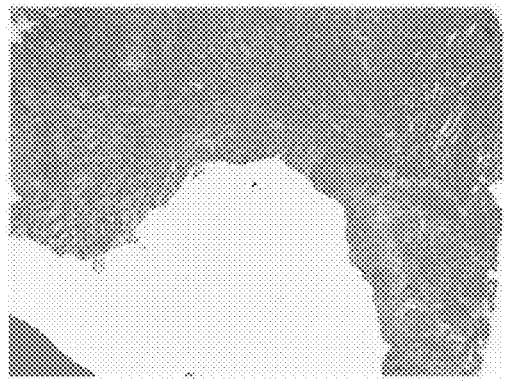

Rabbits as treated in Section 6.1 showed variation in myocardial morphology as exhibited by Hemotoxylin and Eosin staining. The control rabbits have a distorted myocardial morphology (FIG. 2A) while the rabbits treated with liposomal alendronate exhibit a more normal morphology (FIG. 2B).

6.3 Effect of Liposomal Alendronate on Macrophage Infiltration

Figure 3A:
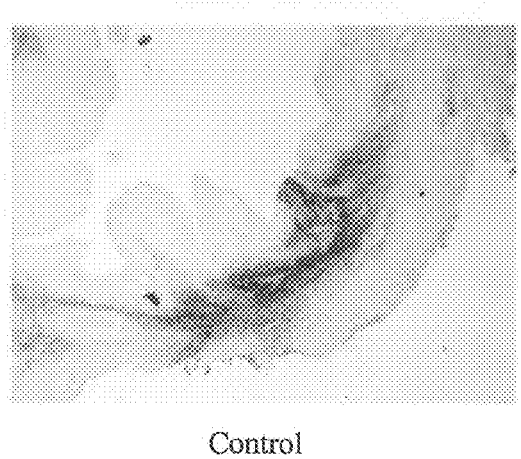
FIGS. 3A-3B illustrate the reduction in macrophage infiltration following treatment with liposomal alendronate after reversible coronary occlusion in rabbits. Control rabbits (A) show increased RAM11+ macrophage accumulation in the zone of infarct as compared to rabbits treated with liposomal alendronate (B).
Figure 3B:
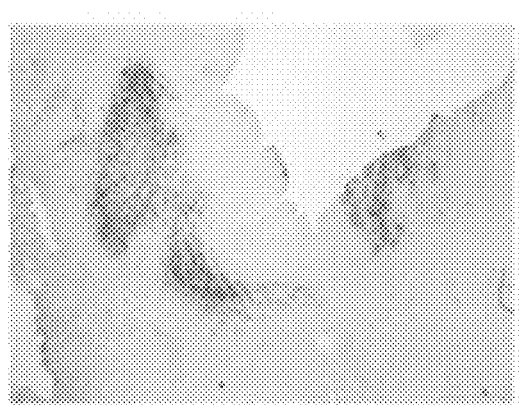

Rabbits as treated in Section 6.1 showed a reduction in macrophage infiltration in rabbits treated with liposomal alendronate. Representative sections of the rabbits' hearts were subjected to immunostaining for RAM11+ macrophages. Sections from rabbits treated with liposomal alendronate (FIG. 3B) showed less staining and therefore had less RAM11+ macrophages accumulation than sections from control rabbits (FIG. 3A).

Liposomal alendronate was also shown to reduce the number of circulating monocytes systemically. Rabbits were administered saline (control) or liposomal alendronate (3 mg/kg, i.v.) Monocyte levels in circulating blood were determined using FACS analysis for CD-14. At 48 hours after injection with liposomal alendronate, the blood monocyte population was reduced by 75-95% as compared to the control group.

We claim:

1. A method of treating unstable angina comprising administering an effective amount of a formulation to a patient in need thereof, said formulation comprising a bisphosphonate which is encapsulated in a particle, embedded in a particle, or in a particulate, said particle or particulate having a size of 0.05 to 1.0 microns, wherein said bisphosphonate is phagocytosed and acts intracellularly, thereby decreasing phagocytic cell activity.

2. A method of treating unstable angina comprising administering an effective amount of a formulation to a patient in need thereof, said formulation comprising a bisphosphonate which is encapsulated in a particle, embedded in a particle, or in a particulate, said particle or particulate having a size of 0.05 to 1.0 microns, wherein said bisphosphonate is phagocytosed and acts intracellularly, thereby decreasing phagocytic cell numbers.

3. A method of treating unstable angina comprising administering an effective amount of a formulation to a patient in need thereof, said formulation comprising a bisphosphonate which is encapsulated in a particle, embedded in a particle, or in a particulate, said particle or particulate having a size of 0.05 to 1.0 microns and said formulation inhibiting macrophages or monocytes.

4. A method of treating unstable angina comprising administering an effective amount of a formulation to a patient in need thereof, said formulation comprising a bisphosphonate encapsulated in a liposome, said liposome having a size of 0.05 to 1.0 microns, and said bisphosphonate acting intracellularly, thereby decreasing phagocytic cell activity.

5. The method of any one of claims 1-4, wherein said unstable angina is caused by the formation of a blood clot in a coronary artery at the site of a ruptured plaque.

6. The method of any one of claims 1-4, wherein said formulation is administered to a patient at increased risk of plaque rupture.

7. The method of any one of claims 1-4, wherein said formulation causes the stabilization of an unstable plaque accumulation.

8. The method of any one of claims 1-4, wherein said bisphosphonate comprises a compound having formula (I):

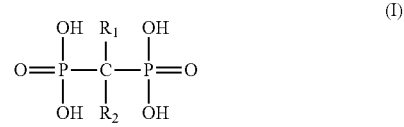

wherein R1 is H, OH or halogen group; and

R2 is halogen; linear or branched C1-C10 alkyl or C2-C10 alkenyl, optionally substituted by heteroaryl or heterocyclyl C1-C10 alkylamino or C3-C8 cycloalkylamino; —NHY where Y is hydrogen, C3-C8 cycloalkyl, aryl or heteroaryl; or —SZ, where Z is chlorosubstituted phenyl or pyridinyl.

9. The method of any one of claims 1-4, wherein said bisphosphonate is selected from the group consisting of clodronate, etidronate, tiludronate, pamidronate, alendronate and risendronate.

10. The method of any one of claims 1-4, wherein multiple therapeutic agents are contained in the formulation, and wherein at least one of the therapeutic agents comprises a bisphosphonate.

11. The method of any one of claims 1-3, wherein said bisphosphonate is encapsulated in a liposome.

12. The method of any one of claims 1-3, wherein said bisphosphonate is embedded in a carrier selected from the group consisting of microparticles, nanoparticles, microspheres, and nanospheres.

13. The method of any one of claims 1-3, wherein said bisphosphonate is formulated as a particulate selected from the group consisting of aggregates, flocculates, colloids, polymer chains, insoluble salts and insoluble complexes.

14. The method of any one of claims 1-3, wherein said bisphosphonate is encapsulated in a particle and said particle comprises cholesterol.

15. The method of claim 4, wherein said liposome comprises cholesterol.

* * * * *